United States Patent [19]

Pugach

[11] Patent Number: 4,605,541

[45] Date of Patent: Aug. 12, 1986

[54] RECOVERY OF NOBLE METAL VALUES FROM CARBONYLATION RESIDUES USING IMMISCIBLE LIQUIDS

[75] Inventor: Joseph Pugach, Ridgewood, N.J.

[73] Assignee: The Halcon SD Group, Inc., Montvale, N.J.

[21] Appl. No.: 768,992

[22] Filed: Aug. 26, 1985

[51] Int. Cl.$^4$ ............................................. C01G 55/00
[52] U.S. Cl. ........................................ 423/22; 502/24; 260/546; 260/549
[58] Field of Search ........................... 423/22; 502/24; 260/546, 549

[56] References Cited

U.S. PATENT DOCUMENTS

| | | | |
|---|---|---|---|
| 4,434,240 | 2/1984 | Pugach | 502/24 |
| 4,440,570 | 4/1984 | Erpenbach et al. | 260/549 |
| 4,442,304 | 4/1984 | Erpenbach et al. | 502/24 |
| 4,473,655 | 9/1984 | Tsunoda et al. | 502/24 |
| 4,557,760 | 12/1985 | Erpenbach et al. | 502/24 |

*Primary Examiner*—H. T. Carter
*Attorney, Agent, or Firm*—Harold N. Wells

[57] ABSTRACT

Heavy residues produced by noble metal catalyzed carbonylation reactions and containing Group VIII noble metals, particularly rhodium, are treated with a mixture of immiscible liquids to precipitate solids containing substantially all of the noble metal contained in the residues. The solids may be returned directly for reuse in the carbonylation reaction. One group of liquids consists of water with immiscible alcohols or hydrocarbons, or mixtures thereof. A second group consists of acetic anhydride with immiscible hydrocarbons.

9 Claims, No Drawings

RECOVERY OF NOBLE METAL VALUES FROM CARBONYLATION RESIDUES USING IMMISCIBLE LIQUIDS

PRIOR ART

The invention relates to the carbonylation processes in which carbon monoxide is reacted with esters or ethers to produce anhydrides or higher molecular weight products. More specifically, the invention relates to the recovery for reuse of the noble metal values from residues formed in such carbonylation processes.

The carbonylation processes of interest differ from hydroformylation processes commonly employed industrially. Typically, in hydroformylation carbon monoxide and hydrogen are reacted with olefins to form higher molecular weight aldehydes and alcohols.

Both hydroformylation and carbonylation processes may produce heavy residues which must be removed to avoid detrimental effects on the reaction. The nature of these residues is not always precisely disclosed in the art, but they are thought to be polymers of the reaction products and/or byproducts. The chemical nature of the residues and their ability to hold the noble metal-containing catalyst would be expected to relate to the type of reaction being carried out. Thus, recovering the noble metal values from such residues will require methods particularly suited to the origin of the residues. The methods to be disclosed herein are especially useful with respect to the processes described in U. S. Pat. Nos. 4,340,569; 4,340,570; and 4,341,741.

Recovery of noble metal values from hydroformylation residues is disclosed in a number of patents, which may reflect the extensive industrial applications of hydroformylation. However, since the residues are chemically related to the reactants, these patents are not considered as pertinent to the present invention as those pertaining to carbonylation generally or, more specifically, to the carbonylation of esters and ethers to form anhydrides.

Some disclosed methods for recovering noble metals from carbonylation processes have been directed to processes in which the presence of heavy residues has not been mentioned.

U.S. Pat. No. 3,887,489 discloses the recovery of rhodium from carbonylation processes which employ rhodium halide carbonyl complexes. Rhodium is precipitated from spent catalyst solutions by heating to 100°–190° C., preferably in the presence of an alkyl alcohol, and thereafter converted to an active form for reuse. It should be noted that the process appears to have been applied to carbonylation of methanol to acetic acid, which produces no heavy residues. The principal objective of the rhodium recovery process was the separation from metallic corrosion products.

U.S. Pat. No. 4,131,640 presents still another method of precipitating rhodium from a rhodium carbonyl complex used for carbonylation of an alkanol or an olefin. The rhodium is deposited on a solid carrier, which is then treated to convert the rhodium back into a carbonyl complex. The precipitation occurs as a result of hydrogenation of the initial rhodium-containing solution at 20°–300° C. Again, the technique is used in carbonylation reactions which apparently produce a homogeneous product mixture and formation of residues is not noted.

In U.S. Pat. No. 4,442,304 the rhodium content of a catalyst solution obtained in the carbonylation of methyl acetate and/or dimethyl ether is separated by treating the solution with water, which dissolves the quaternary nitrogen or phosphorus compounds used as promoters in the process. The precipitate is subsequently treated with aliphatic ethers to remove the organic contaminants. In an apparently related patent, U.S. Pat. No. 4,440,570, the water treatment of the '304 patent is used, but the precipitated residue is to be refined to recover the noble metal.

Residues from a carbonylation process for preparing acetic anhydride may be treated with methyl iodide and aqueous hydrogen iodide to extract rhodium, as disclosed in U.S. Pat. No. 4,388,217. Such a process provides a solution of rhodium, rather than a solid containing it. A similar process is disclosed in Belgian Patent No. 891,231.

A solution containing dissolved rhodium derived from the reaction of carbon monoxide and hydrogen with alcohols may be treated with a crown ether, an alkaline cesium salt and water to recover the rhodium by precipitation, as shown in U.S. Pat. No. 4,363,765.

Still another method of removing rhodium from a carbonylation solution is found in EP No. 18102. Silica and a silicon compound are reacted to form a product capable of absorbing rhodium from a solution.

A two-step separation of volatile materials from a carbonylation reaction mixture is shown in EP No. 81732. No treatment for recovery of the rhodium content is applied prior to recycle of the residual liquid.

The recovery of rhodium or other noble metal catalysts from the residues formed in the carbonylation of esters or ethers to form anhydrides has been the subject of commonly-assigned U.S. Pat. Nos. 4,340,569; 4,340,570; 4,341,741; 4,476,237; 4,476,238; and 4,434,240. In U.S. Pat. Nos. 4,340,569; 4,340,570; and 4,341,741 residues are treated with amines to facilitate subsequent extraction of the rhodium with aqueous acids. In U.S. Pat. No. 4,343,240 the residues are given chemical treatments to precipitate solids which contain substantially all of the rhodium, leaving the depleted residues for disposal. It was suggested that diluents such as methanol, glyme, and isopropanol could be used to dilute the residues prior to treatment with reagents to precipitate solids. However, such diluents did not in themselves result in precipitation under the conditions employed.

U.S. Pat. Nos. 4,476,237 and 4,476,238 pertain to the use of selective extraction to remove heavy residues preferentially, leaving rhodium behind. The preferred solvents had relatively poor solvent properties, and isopropanol and ethanol were shown to be such effective solvents that they were not selected.

In co-pending application U.S. Ser. No. 752,697 certain classes of liquids are shown to precipitate substantially all of the rhodium which the residues contain. Of particular interest are aliphatic alcohols, carboxylic acids, and esters of such acids.

The present invention is directed to improved techniques by which such residues may be treated to recover their noble metal content using mixtures of immiscible liquids.

SUMMARY OF THE INVENTION

Group VIII noble metals, typically rhodium, are recovered from the heavy residues of the noble metal catalyzed carbonylation reactions in which esters and ethers are combined with carbon monoxide to form anhydrides or other higher molecular weight products. The residue is separated from the carbonylation reaction mixture and then treated at above ambient temperatures with a mixture of immiscible liquids capable of precipitating solids which contain substantially all of the noble metal contained in the residues. The solids may be further treated to recover the noble metals, but they may be returned directly to the carbonylation reactor and reused without further preparation. If substantially all of the noble metal is found in the solids and very little in the two liquid phases, the liquids may be either returned directly to the carbonylation reactor (if compatible), treated to recover noble metal, or disposed of without additional recovery.

One group of immiscible liquids consists of water with aliphatic alcohols or hydrocarbons (aliphatic or aromatic) or mixtures thereof. A second group consists of acetic anhydride with hydrocarbons (aliphatic or aromatic). Of the aliphatic alcohols, those having 4 to 15 carbon atoms, particularly 4 to 8 carbon atoms, are preferred. Generally, the aliphatic hydrocarbons should have 5 to 20 carbon atoms, n-octane and cyclohexane having been found to be particularly useful. The aromatics typically will have an alkyl-substituted benzene ring in which the substituted groups have 1 to 10 carbon atoms.

DESCRIPTION OF THE PREFERRED EMBODIMENTS

The recovery of Group VIII noble metals, especially rhodium, from carbonylation and hydroformylation reaction mixtures has been of considerable interest to those skilled in the art. Of particular concern to the present inventor is the recovery of Group VIII noble metals, particularly rhodium, from catalysts used in the carbonylation of a carboxylic ester or an alkyl ether to an anhydride, or to higher molecular weight products, especially the carbonylation of methyl acetate or dimethyl ether to acetic anhydride. In another aspect, the invention relates to recovery of rhodium-lithium catalysts used for the carbonylation in the presence of hydrogen of methyl acetate and/or dimethyl ether to ethylidene diacetate. These processes have been described in depth in British Patent Nos. 1,468,940 and 1,538,782, and are summarized in U.S. Pat. Nos., 4,340,569; 4,340,570; and 4,341,741.

The invention broadly relates to the selective removal of the noble metals by precipitation from the heavy high-boiling residues, produced by carbonylation reactions, with or without hydrogen being present. These heavy residues are complex, and their chemical composition is not fully characterized. Where they have been produced during the carbonylation of esters or ethers, they are known to contain high molecular weight compounds with organic carbonyl and acetate functions. If a sample of a carbonylation reaction mixture is flashed and concentrated, the residues which are recovered typically contain up to about 4 percent by weight rhodium after the volatile constituents have been removed.

The carbonylation reaction mixture typically produces high-boiling residues which may be tolerated, but which cannot be allowed to accumulate indefinitely. The rate at which the residues are produced and their composition will depend upon many factors, not fully understood at this time. The rate at which the residues should be removed and the level to which they are permitted to accumulate in the reaction mixture are established empirically for a particular reaction system. Typically, the reactor will be operated so that the products and other light materials will be flashed off—either from the reacting mixture itself or from a slipstream which is recycled to the reactor. In either case, heavier materials not flashed off accumulate, and a portion of these materials is separated and then concentrated to leave only the heaviest materials, which are then treated to precipitate the noble metal values according to the methods of the invention. After the noble metals have been removed, the residues may be purged.

In its broadest aspect, the invention comprises a process for recovering Group VIII noble metals from the residues of noble metal catalyzed carbonylation reactions in which esters and ethers are combined with carbon monoxide to form anhydrides or other higher molecular weight products. The process separates the residues from the carbonylation reaction mixture and then treats the residue with a suitable reagent capable of precipitating a solid containing substantially all of the noble metal content of the residue.

Separation of the residue from the carbonylation reaction mixture may be carried out by flashing of the mixture to a lower pressure and then returning the vapors to the reactor system. This may be done with the net reactor product or with a slipstream if the products are removed as vapor from the reactor itself. Any desired degree of concentration may be obtained by flashing to lower pressures. Preferably, the residue will be concentrated until substantially all of the volatile components are removed. The noble metal content will have been increased significantly, say, up to about 4 weight percent.

The precipitation of substantially all of the noble metals from carbonylation residues is carried out by treating with mixtures of immiscible liquids. Water or acetic anhydride will comprise one phase, with immiscible aliphatic or aromatic hydrocarbons or aliphatic alcohols as the second phase. It should be understood that "immiscible" refers to liquids which separate into two layers at room temperature, and does not necessarily imply a complete lack of solubility of one phase in the other, as will be apparent to those familiar with the properties of, for example, higher alcohols and water.

Of the aliphatic hydrocarbons, those having 5-20 carbon atoms are preferred; n-octane and cyclohexane are especially useful.

Of the aromatic hydrocarbons, the alkyl-substituted benzenes in which the substituted groups contain 1-10 carbon atoms are preferred. Toluene, xylene, and ethyl benzene are examples of this group.

Of the aliphatic alcohols, not all are immiscible with water; thus, only those having above 3 carbon atoms are useful, particularly those having 4-8 carbon atoms. The alcohols generally would not be used with acetic anhydride, since they could react to form esters.

The amount of the immiscible liquids used will vary widely depending upon the nature of the residue, the liquids chosen, and the conditions of contacting. In the examples below, an excess of the liquids was used to assure that all the rhodium was precipitated, but it will be understood that in practical applications the amount of reagent employed would be optimized. Above ambient temperatures are believed necessary for best recovery of rhodium. The contacting typically has been carried out in the examples at the atmospheric pressure boiling temperature of the treated mixture, with condensation and reflux of the volatile materials to maintain the liquid composition. Typically, such reflux temperatures will be about 50° C. to 250° C. for the most useful reagents. However, temperatures above and below the reflux temperature have been found to give acceptable results. It would be expected that an optimum temperature would be determined for practical applications of the invention. The pressure may be any suitable value, depending upon the temperature and the constituents of the system.

found to contain 3.2% rhodium, equaling more than 99.6% of the rhodium in the original residue. The rhodium remaining in the cyclohexane layer is less than 3 ppm by weight, while that in the water layer also is less than 3 ppm by weight. The lithium salts are predominantly found in the water phase.

The above results, along with those of other hydrocarbon-water and aclohol-water mixtures tested in a similar manner, are summarized in the following table

TABLE A

| Residue gms | Water gms | Solvent | gms | Precipitate gms | % Rh (wt) | Rhodium wt ppm Water | Rhodium wt ppm Solvent | Rhodium Recovery % |
|---|---|---|---|---|---|---|---|---|
| 10 | 20 | Cyclohexane | 20 | 2.9 | 1.5 | <3 | 6 | 99.6 |
| 10 | 20 | n-octane | 20 | 2.1 | 2.1 | <7 | <5 | 99.4 |
| 10 | 20 | Toluene | 20 | 0.68 | 6.8 | <5 | 62 | 97.3 |
| 10 | 20 | n-pentanol | 20 | 0.62 | 7.6 | <4 | 46.9 | 97.3 |
| 10 | 20 | n-hexanol | 20 | 0.64 | 7.5 | <3 | 49.7 | 97.2 |
| 10 | 20 | n-octanol | 20 | 0.61 | 7.8 | <4 | 37.9 | 98.0 |
| 10 | 20 | 4 methyl 2 pentanol | 20 | 0.72 | 6.7 | <3 | 62.8 | 90.2 |

Reflux time = 6 hours

Various embodiments of the invention are illustrated in the following examples, in which the residue was obtained from carbonylation reactions of which the following is a representative description.

In a continuous reaction, acetic anhydride is produced by the carbonylation of methyl acetate in the presence of methyl iodide, carbon monoxide, and hydrogen. The reaction is catalyzed by the mixture of rhodium trichloride trihydrate and lithium iodide, which are added to the initial charge placed in the reactor in amounts sufficient to provide about 0.01 mol Rh/liter of liquid in the vessel and 0.5 mol Li/mol Rh. The reaction is operated at about 180° C., 55 kg/cm² absolute, with partial pressures of about 35 kg/cm² CO and about 5-6 kg/cm² H$_2$. The product acetic anhydride is obtained as a vapor by flashing a withdrawn stream of the reacting mixture. The remaining liquid is recycled to the reactor. The liquid recycled after flashing contains about 4 weight percent methyl iodide, 7 weight percent methyl acetate, 32 weight percent acetic anhydride, 24 weight percent acetic acid, with about 1-10 weight percent heavy residues. A slipstream is withdrawn from the recycle stream at a rate sufficient to maintain the residues in the reactor at an acceptable level. The residue-containing liquid which remains after the gases have been separated is concentrated and treated to precipitate substantially all of its rhodium content before disposal of the residue.

EXAMPLE 1

Mixtures Containing Water

A 15-gm sample of a concentrated residue containing 0.3% rhodium, along with lithium salts and iodine compounds, is combined with 30 gms of cyclohexane and 30 gms of water and refluxed at atmospheric pressure for 6 hours. A precipitate weighing 1.4 gms is recovered and

EXAMPLE 2

Mixtures Containing Acetic Anhydride

Samples of the concentrated residues are treated with mixtures of acetic anhydride and hydrocarbons in the manner of Example 1 to precipitate solids containing rhodium, as summarized in the following table.

TABLE B

| Residue gms | Acetic Anhydride gms | Solvent | gms | Precipitate gms | % Rh (wt) | Rhodium wt ppm Acetic Anhydride | Rhodium wt ppm Solvent | Rhodium Recovery % |
|---|---|---|---|---|---|---|---|---|
| 15 | 40 | n-octane | 40 | 2.3 | 2.2 | 17 | <10 | 97.7 |

Reflux time = 6 hours

The lithium salts are only partially soluble in acetic anhydride, so that some remain in the precipitate.

EXAMPLE 3

(Comparative)

Although water and acetic anhydride have been shown above to produce similar results when employed in immiscible mixtures, their performance individually is quite different, as the following results show.

TABLE C

| Residue gms | Liquid | gms | Reflux hrs | Precipitate gms | % Rh (wt) | Rhodium in Solvent wt ppm | Rhodium Recovery % |
|---|---|---|---|---|---|---|---|
| 20 | Acetic Anhydride | 80 | 6 | 4.6 | 0.06 | 755 | 3.9 |
| 10 | Water | 60 | 6 | 5.4 | 0.6 | <3 | >99.4 |

Water is shown in Table C to remove a portion of the residue, but to leave substantially all of the rhodium in the solid phase. It has the disadvantage of leaving a precipitate which is relatively dilute in rhodium, making further recovery more difficult and expensive. When selected immiscible solvents are added, Table A shows that much more concentrated precipitates are obtained, without loss of substantial amounts of rhodium.

Acetic anhydride acts in a different manner. It is capable of dissolving essentially all of the rhodium in the residue, making it completely unsuitable for recovering rhodium in a solid phase. However, when an immiscible solvent is added, the rhodium remains with the solids, and very little appears in either of the solvent phases, as Table B shows. This reversal of solubility is not always found. For example, when methanol is used alone, essentially all of the rhodium is taken up by the methanol, as is the case when acetic anhydride is used alone. However, when n-octane is added to methanol, the methanol phase still contains most of the rhodium, while only a minor fraction is recovered in the solid phase.

As the above examples show, by selecting as one solvent acetic anhydride or water, and as the second solvent an aliphatic alcohol, aliphatic hydrocarbon, or an aromatic hydrocarbon, it is possible to precipitate substantially all of the rhodium in a concentrated solid phase, while leaving only a small amount in the two liquid phases. Recovery of residual rhodium from the liquids may be done, but it may be economically feasible merely to dispose of them. The rhodium-containing solids may be further concentrated if desired, but they may be returned to the carbonylation reaction for further use. Effectively, then, the rhodium has been recovered and the heavy organic residues have been separated for disposal. The lithium salts generally will have been transferred, at least in part, to the water or acetic anhydride phases. They may be returned to the carbonylation mixture for reuse.

What is claimed is:

1. A process for recovering rhodium from the high molecular weight residues formed in rhodium-lithium catalyzed carbonylation reactions in which esters and ethers are combined with carbon monoxide in the presence of iodides to form anhydrides, comprising:
   (a) separating and concentrating the residue from the carbonylation reaction mixture by removing volatile components thereof;
   (b) treating at temperatures above ambient the separated residue of (a) with a mixture of immiscible liquids capable of precipitating a solid containing substantially all of the rhodium content of said residue and consisting of immiscible mixtures of water with aliphatic alcohols or hydrocarbons or mixtures thereof or immiscible mixtures of acetic anhydride with hydrocarbons; and
   (c) separating the precipitated solid of (b).

2. A process of claim 1 further comprising:
   (d) returning said solid to the carbonylation reaction mixture for reuse.

3. A process of claim 1 wherein said treatment is carried out at a temperature in the range of 50° C. to 250° C.

4. A process of claim 1 wherein said aliphatic alcohols have from 4 to 15 carbon atoms.

5. A process of claim 4 wherein said alcohols have from 4 to 8 carbon atoms.

6. A process of claim 1 wherein said aliphatic hydrocarbon has from 5 to 20 carbon atoms.

7. A process of claim 6 wherein said aliphatic hydrocarbon is n-octane or cyclohexane.

8. A process of claim 1 wherein said aromatic hydrocarbon is an alkyl-substituted benzene having 1–10 carbon atoms in the substituted groups.

9. A process of claim 8 wherein said aromatic hydrocarbon is at least one of the group consisting of toluene, xylene, and ethyl benzene.

* * * * *